United States Patent
Swanson

(10) Patent No.: US 7,604,639 B2
(45) Date of Patent: Oct. 20, 2009

(54) PATELLAR CUTTING GUIDE

(75) Inventor: Todd V. Swanson, Las Vegas, NV (US)

(73) Assignee: Smith & Nephew, Inc., Memphis, TN (US)

( * ) Notice: Subject to any disclaimer, the term of this patent is extended or adjusted under 35 U.S.C. 154(b) by 68 days.

(21) Appl. No.: 11/374,798

(22) Filed: Mar. 14, 2006

(65) Prior Publication Data

US 2006/0161165 A1 Jul. 20, 2006

Related U.S. Application Data

(63) Continuation of application No. 10/143,203, filed on May 10, 2002, now Pat. No. 7,048,741.

(51) Int. Cl.
*A61B 17/58* (2006.01)
*A61F 2/00* (2006.01)
(52) U.S. Cl. .......................... 606/88; 606/87
(58) Field of Classification Search .............. 606/79, 606/80, 85, 87, 88, 89, 86 R, 82, 83, 84; 623/20.14, 623/20.15, 20.18, 20.19
See application file for complete search history.

(56) References Cited

U.S. PATENT DOCUMENTS

| | | | | |
|---|---|---|---|---|
| 4,565,192 | A | * | 1/1986 | Shapiro ................. 606/82 |
| 4,944,756 | A | | 7/1990 | Kenna |
| 5,108,401 | A | * | 4/1992 | Insall et al. ............. 606/79 |
| 5,425,775 | A | | 6/1995 | Kovacevic et al. |
| 5,658,293 | A | | 8/1997 | Vanlaningham |
| 5,667,512 | A | * | 9/1997 | Johnson ................ 606/88 |
| 6,056,754 | A | | 5/2000 | Haines et al. |
| 6,174,314 | B1 | | 1/2001 | Waddell |
| 6,190,390 | B1 | | 2/2001 | McAllister |
| 6,342,075 | B1 | | 1/2002 | MacArthur |
| 6,514,259 | B2 | | 2/2003 | Picard et al. |
| 6,551,325 | B2 | | 4/2003 | Neubauer et al. |
| 6,702,821 | B2 | | 3/2004 | Bonutti |
| 6,855,150 | B1 | * | 2/2005 | Linehan ................ 606/96 |

(Continued)

OTHER PUBLICATIONS

Health Education Video Unit; *Total Knee Replacement Still*; Dec. 2001; http://www.hevu.org.uk/products/distrib/knee/index.html., 1 page.

(Continued)

*Primary Examiner*—Pedro Philogene
(74) *Attorney, Agent, or Firm*—Weide & Miller, Ltd.

(57) ABSTRACT

A patellar cutting guide is particularly useful in a method of minimally invasive knee arthroplasty in which an incision is made along the medial or lateral aspect of a patient's knee, exposing the knee joint. The patellar cutting guide includes a clamp configured to be located exterior to the knee over the anterior portion of the patella, a stop having at least one portion configured to extend through an incision to a location posterior to the patella, and a cutting guide defining a cutting slot. The clamp may have outwardly extending spikes for passage through the tissue overlying the patella and into engagement with the patella. The stop is movable relative to the clamp and/or cutting guide. In one embodiment, the cutting guide is offset laterally and posteriorly relative to the clamp so that the slot is aligned with a medially or laterally-formed incision in the knee.

16 Claims, 7 Drawing Sheets

U.S. PATENT DOCUMENTS

| | | |
|---|---|---|
| 7,048,741 B2 | 5/2006 | Swanson |
| 2003/0158606 A1 | 8/2003 | Coon et al. |

OTHER PUBLICATIONS

Joint Replacement Instrumentation Limited; *Products: The Furlong H-A.C. Total Knee Replacement Tibial Tray*; Dec. 2001; http//www.jri-ltd.co.uk/html/product_7.htm, 2 pages.

Smith & Nephew, Inc.; *Orthopaedic Division Products: Knee Products: Genesis Total Knee System*; Oct. 2001, http://www.smithnephew.com/orthopaedics/products. , 1 page.

Johnson&Johnson Gateway, LLC; *Surgical Technique: LCS Mobile Bearing Total Knee System Surgical Techinque Using Milestone Instruments*; Oct. 2001; http://www.jnjgateway.com. 35 pages.

Johnson&Johnson Gateway, LLC; *Microsites Display: DePuy Mobile Bearing Knee Microsite*; Oct. 2001; http://wwwjnjgateway.com., 2 pages.

DePuy; Inc.; *Knee Replacement*; Oct. 2001; http://www.depuy.com/knee/knee-print.cfm, 7 pages.

DePuy, Inc.; *AMK Total knee System*; Oct. 2001; http:.//www.depuy.com, 1 page.

\* cited by examiner

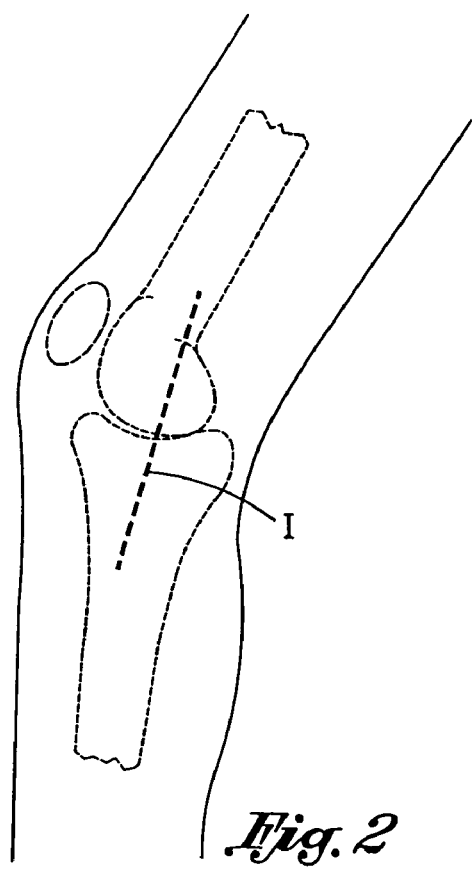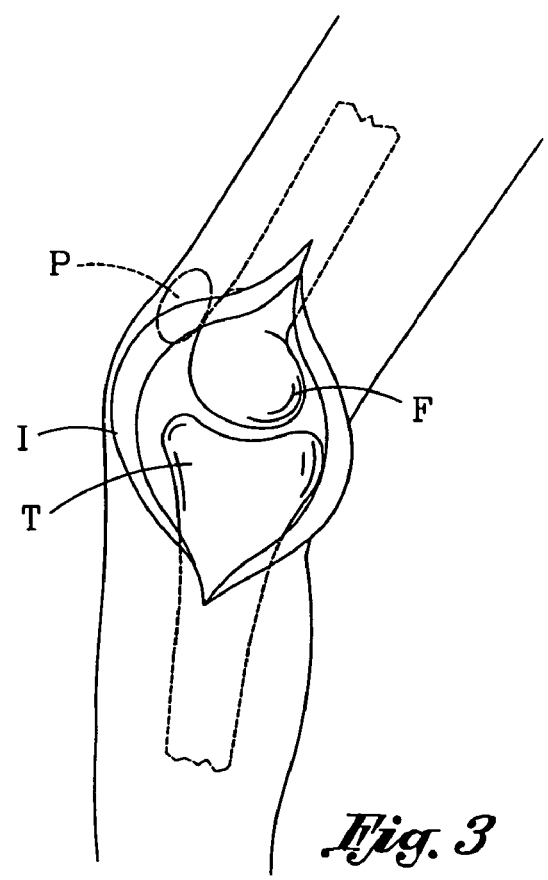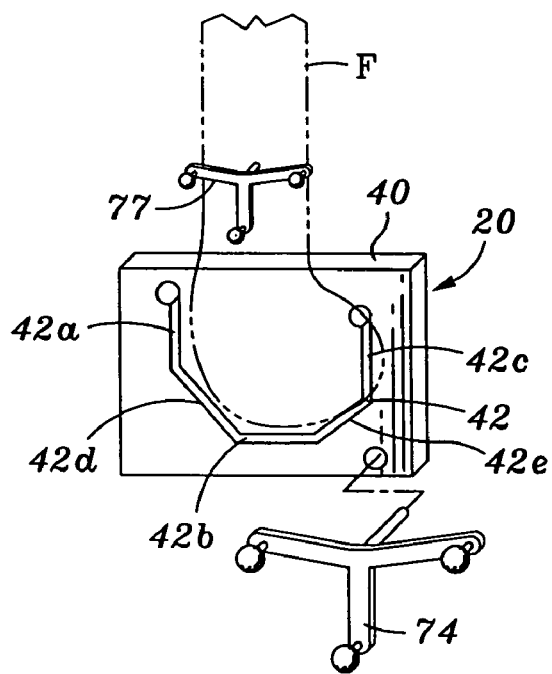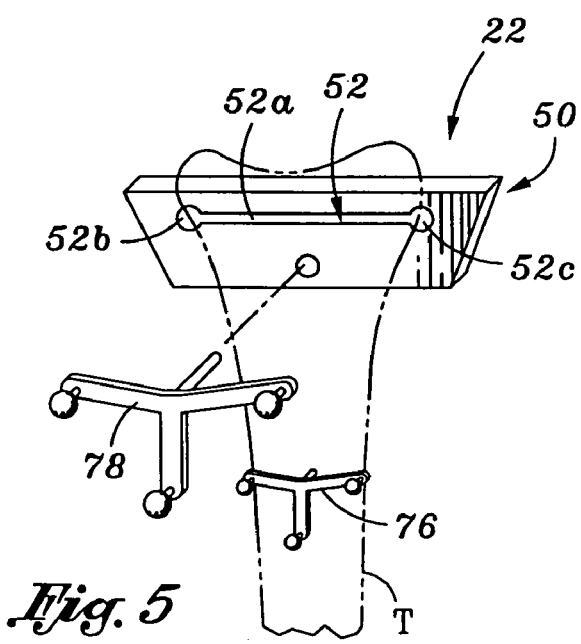
Fig. 2
Fig. 3
Fig. 4
Fig. 5

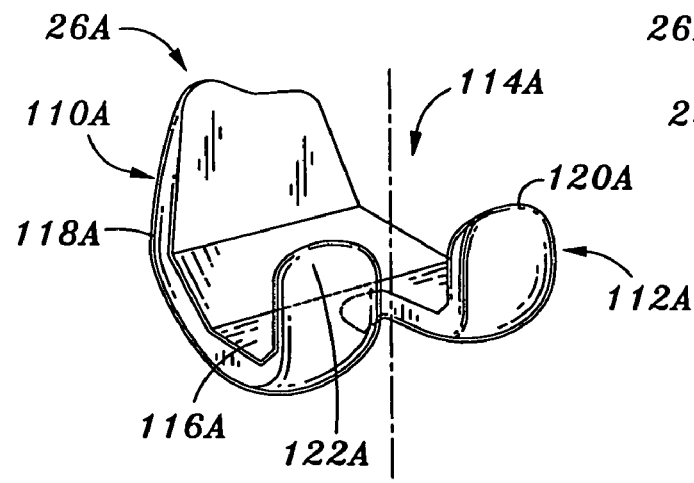
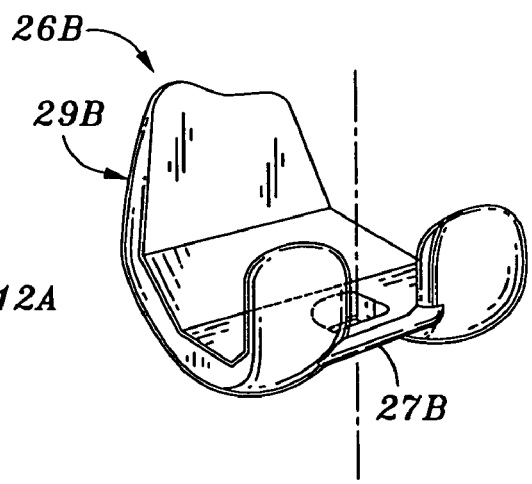
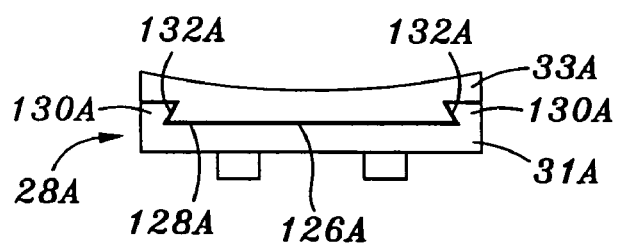
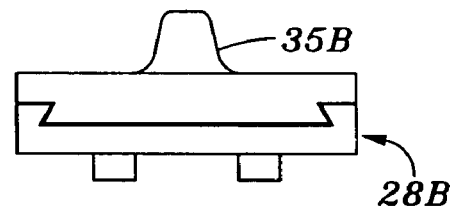
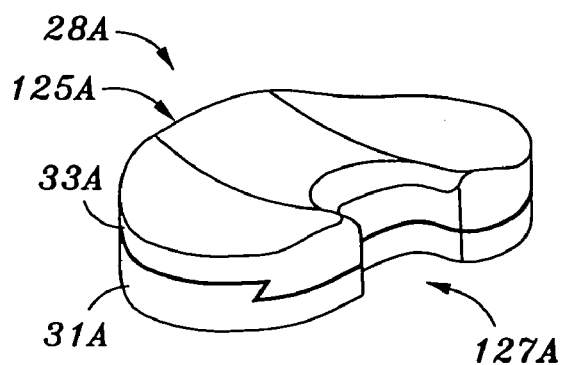
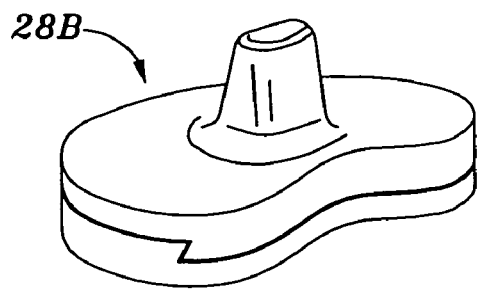

PATELLAR CUTTING GUIDE

RELATED APPLICATION

This application is a continuation of U.S. application Ser. No. 10/143,203 filed May 10, 2002, now U.S. Pat. No. 7,048,741.

FIELD OF THE INVENTION

The present invention relates to methods and apparatus for total knee arthroplasty.

BACKGROUND OF THE INVENTION

Total knee replacement (also known as total knee arthroplasty) surgery is a common procedure that is performed on hundreds of thousands of people each year. A number of circumstances may require replacement of a person's knee. For example, excessive deterioration of knee cartilage may necessitate knee replacement. This type of problem and other injuries to the knee may result from accidents, disease such as osteo-arthritis or rheumatoid arthritis, or other causes.

The knee joint or "knee" is formed by the bottom or distal end of the femur (or "thigh bone") which extends from the hip, the top or proximal end of the tibia (or "shin bone") which extends to the ankle, and the patella (or "knee cap"). The distal end of the femur and the proximal end of the tibia are covered by a smooth layer of cartilage which allows the femur and tibia to move smoothly against each other. The patella also has a smooth cartilage layer on its posterior surface to allow smooth motion against the femur. However, certain conditions, most commonly arthritis, can cause permanent deterioration of the cartilage. When the cartilage wears away, the roughened surfaces of the femur, tibia and patella may rub against each other causing pain, stiffness and swelling.

One option for treating the permanent deterioration of the cartilage is total knee replacement surgery. In a total knee replacement procedure the end surfaces of the tibia and femur, and the posterior surface of the patella, are resurfaced. Generally, the surface that covers the femoral section is made from smooth metal or ceramic, while the surface attached to the tibia is constructed of metal and a high-density polyethylene. The patella is also resurfaced with a high-density polyethylene.

The commonly known method for total knee replacement is illustrated in FIGS. 1A-1D. Illustrated in FIG. 1A is a front exterior view of a knee. The femur F, tibia T and patella P are illustrated in phantom view. In accordance with the existing total knee replacement procedure, an 8 to 12 inch incision I is made over the anterior or front portion of the knee.

Next, as illustrated in FIG. 1B, the 8-12 inch anteriorly located incision is opened exposing the patella and retinacular tissue R attached to both sides of the patella. The medial patellar retinaculum is incised, thereby allowing for the eversion of the patella P. With flexion of the knee, the patella falls posteriorly out of the way so that the interior of the kneejoint is completely exposed.

Next, the distal end of the femur F, the proximal end of the tibia T, and the posterior surface of the patella are machined for acceptance of replacement knee components. In general, this step comprises affixing a cutting guide to the femur, tibia and patella, respectively, and utilizing a cutting apparatus to remove a thin layer of the arthritic surface of the femur, tibia, and patella. Further, anterior dislocation of the tibia from the femur is required to prepare the tibia. As is well known, these steps are rather exacting and requires precision if proper resection of the femur, tibia and patella is to be successful.

Knee replacement components are then connected to the tibia T and femur F as illustrated in FIG. 1C. Positioning occurs by instruments that reference external landmarks or the intramedullary canal of the femur F and tibia T. As illustrated, the components include a femoral component FC which is connected to the femur F. The femoral component FC generally has an inner surface and outer surface. The inner surface abuts the distal end of the femur F, and may include one or more elongate pegs or a box for impacting into the femur F. The femoral component is generally attached to the end of the femur using a special acrylic bone cement, or by obtaining a tight "press fit" of the femoral component FC to the femur F. The outer surface of the femoral component FC comprises one of the replacement knee surfaces.

The components also include a tibial component TC. This component has an inner surface and outer surface. The inner surface again mates to the tibia T, and as such may include a stem for impacting into the tibia T. As illustrated, the stem is somewhat long and driven into engagement by guiding the tibial component TC along the axis of the tibia T into engagement with the proximal end of the tibia T. Because of the elongated tibial stem, the tibia must be dislocated anterior to the femur for insertion of the tibial component. The tibial component TC is generally attached to the upper end of the tibia using bone cement or screws. The outer surface of the tibial component TC attaches to a high-density polyethylene insert which comprises the other of the replacement knee surfaces.

Though not illustrated, with the patella P in an everted position and exposed, the posterior of the patella P may be removed as well. A replacement patella component may be affixed to the rear of the patella P, again using bone cement.

FIG. 1D illustrates the assembled total knee replacement. As illustrated, the femoral component FC rests upon the tibial component TC. Relative motion is permitted between these two components, while at the same time protecting the femur F and tibia T. The patellar component PC glides along the femoral component with knee motion.

The existing method of total knee replacement illustrated in FIGS. 1A-1D has a number of disadvantages. One significant problem is that the procedure is quite invasive and traumatizing. The procedure results in a large incision and substantial stresses upon the body resulting in long periods of recovery/rehabilitation, and extended periods of hospitalization.

In particular, as can be seen, in order to resect the femur and tibia, and to provide sufficient access to the distal end of the femur and proximal end of the tibia, the patella must not only be moved, but everted. The patella is connected to the quadriceps tendon and muscle proximally and to the patellar ligament distally, comprising the extensor mechanism. The extensor mechanism must be stretched in order to permit the patella to be displaced and everted so as to provide frontal access to the knee. This stretching results in substantial strain and traumatization to the extensor mechanism and quadriceps muscle which takes a great deal of time to recover. In fact, in many instances a patient can not actively extend the knee for several days after the procedure. Additionally, the patellar tendon, on occasion, is ruptured or pulled loose from the tibia due to excessive strain with eversion of the patella. Also, the knee is further traumatized by displacing or dislocating the tibia anterior to the femur for tibial preparation and tibial component insertion. This strains and traumatizes the ligaments of the knee and may result in damage to the adjacent nerves and blood vessels or lead to complication including blood clots, nerve palsy, arterial injury, excessive swelling, fracture or ligament avulsion.

In addition, the size of the incision is dependent on the need to provide frontal access, including eversion of the patella, prepare the bony surface and guide the femoral, tibial and patellar components into engagement with the femur, tibia and patella along axes thereof. Use of a smaller frontal incision places excess tension on the skin, often resulting in skin necrosis or delayed healing. The large incision results in a long period of recovery and generally results in a visible scar.

An improved method and apparatus for total knee replacement is desired.

SUMMARY OF THE INVENTION

The invention comprises a method of total or partial knee arthroplasty which is minimally invasive, and one or more components for performing such a method.

In accordance with a method of the invention total knee arthroplasty is accomplished in a minimally invasive manner through a small medial or lateral incision. In one embodiment, this incision is about 8-12 cm long.

A method and apparatus is provided which permits total knee arthroplasty with minimal trauma to the patient. In accordance with the method, the patella is not everted, nor is the tibia displaced or dislocated. The method of the invention is effectuated through the small medial or lateral incision without the need for access to the intramedullary canals of the femur and tibia, and without the need for clear visualization of common landmarks such as the epicondyles, posterior condylar surfaces, and tibial tubercle.

Apparatus, including cutting guides and implements, are preferably configured to be located or attached along the side of the knee, and not the front, and are further located extra-articular instead of intra-articular. These devices and implements preferably permit preparation of the knee through the small lateral or medial incision and placement of trial and replacement knee components through the lateral or medial incision.

A patellar cutting guide is provided for resecting the patella without dissecting the overlying skin, subcutaneous tissues and bursa from the patella, lessening the chance of skin necrosis from subcutaneous dissection, and lessening the chance of knee tenderness and inability of the patient to kneel after total knee replacement.

In accordance with one embodiment of the invention, the method includes the step of creating an incision generally along the medial or lateral mid-line of the knee of a patient or somewhat anterior or posterior to the medial or lateral mid-line. The incision is shorter in length than that used for the standard anterior approach, and preferably only about 8-12 cm in length. The knee joint of the patient is accessed through this incision.

The distal end of the patient's femur at the knee joint is resected to accept a femoral knee component. Likewise, the proximal end of the tibia at the knee joint is resected to accept a tibial knee component. The patella is also resected to accept a patellar knee component. The femoral knee component is passed through the medial or lateral incision and connected to the resected distal end of the femur. Likewise, the tibial knee component is passed through the incision and connected to the resected proximal end of the tibia. If the patella is resected, the patellar component is passed through the incision and connected to the patella.

One embodiment of the invention comprises a femoral cutting guide which comprises a body having a slot therein for accepting a cutting implement. The femoral cutting guide is designed to be located external to the side of the patient's knee, but guide the cutting implement through the medial or lateral incision during resecting of the femur. Unlike previous apparatus and techniques, the femoral cutting guide does not require eversion of the patella and extensor mechanism, nor require access to the intramedullary canal or clear visualization of the common landmarks.

One embodiment of the invention comprises a tibial cutting guide which comprises a body which defines a cutting slot for a cutting implement. The tibial cutting guide is designed to be located external to the side of the patient's knee, but guide the cutting implement through the medial or lateral incision during resecting of the tibia. Unlike previous apparatus and techniques, the tibial cutting apparatus does not require dislocation or displacement of the tibia from the femur, nor require access to the intramedullary canal or clear visualization of the common landmarks.

One embodiment of the invention comprises a method of resecting the patella without incising the overlying skin, subcutaneous tissues and bursa, and without everting the patella. In one embodiment, the method comprises engaging a first stop with the posterior of the patella and a second stop with the anterior of the patella, locating a cutting guide exterior to the knee adjacent the medial or lateral incision, and passing a cutting implement through the cutting guide and incision to resect the posterior of the patella.

One embodiment of the invention comprises a patellar cutting guide for practicing the method, the cutting guide including a first portion defining a slot for accepting a cutting implement and second and third stop portions. The first portion of the patellar cutting guide is designed to be located external to the patient's knee but guide the cutting implement through the medial or lateral incision during resecting of the patella, while the second portion is designed to abut the posterior of the patella for maintaining patella position during resecting. A third portion of the patellar cutting guide is located exterior to the knee and includes spikes which penetrate the skin, engage the anterior of the patella and press it against the stop for secure location during resecting.

In one embodiment, the femoral knee component is generally "C" shaped and includes a trough-shaped inner surface. The profile of the component is minimized along the inner surface to permit the femoral knee component to be inserted transversely through the medial or lateral incision and aligned with the resected femur, including without substantial dislocation of the femur relative to the tibia. To this end, in one embodiment, one or more engaging pegs extend outwardly from the inner surface for engaging one or more recesses in the femur, the length of the pegs minimized. In one embodiment, the femoral knee component is of the posterior cruciate ligament substituting design and includes a cam for engagement by a post on a mating tibial knee component. In one embodiment, the cam has a low profile, extending between a pair of condyle portions of the component and not extending upwardly into the trough area of the component, again minimizing the profile of the component.

In one embodiment, the tibial component is similarly constructed having a low or small profile to insertion through the medial or lateral incision for impaction onto the proximal surface of the tibia. In this regard, in one embodiment, the tibial component includes one or more pegs of reduced length and a short or absent central stem.

In one embodiment, the tibial component comprises a base and a mating insert. In one embodiment, the base and insert are engageable in a "dove-tail" configuration, the base having a groove and the insert having a mating pin. In a preferred embodiment, the groove and pin extend in a lateral or transverse direction, permitting the insert to be inserted in alignment with the base through the medial or lateral incision.

One embodiment of the apparatus includes an impactor for impacting the tibial knee component and/or femoral knee component into engagement with the tibia/femur. In one embodiment, the impactor is generally "U" shaped and includes a first arm for engaging the tibial or femoral knee component through the incision, and a second arm which is then located exterior to the knee and upon which a force may be applied for transmission to the tibial/femoral knee component.

In one embodiment of the invention, the method is performed with image guidance assistance. An image is obtained of the patient's knee, including the femur, the tibia and patella. The image may be obtained by X-ray, fluoroscopy, CT scanning, or MRI. In one embodiment, no image of the knee is necessary and a pre-recorded 3-dimensional depiction of the knee joint is used, the dimensions based on measurements taken intra-operative.

One or more position sensors are attached to the tibia, femur and/or patella, and/or one or more of the components, guides or other tools. Position data is generated by detectors placed in the operating room using a computerized image guidance system tracking the positions of the one or more sensors. In one embodiment, the position data is compared or correlated to the actual image data or the data obtained from intra-operative measurements for visualization by a surgeon. The position and alignment data may be displayed on a display screen and be used, for example, in assuring proper preparation of the bony cuts of the femur, tibia and patella, positioning and alignment of the femoral and tibial knee components to the femur and tibia, including portions thereof not visible by line of sight through the medial or lateral incision.

In another embodiment, the method is performed without such image guided assistance. In one embodiment, an intra-medullary rod is passed through a small anterior incision of about 1 cm or less in length, and through the patellar tendon into the intra-medullary canal of the femur. A femoral cutting guide is attached to the intra-medullary rod to allow it to align with the distal femur through the medial or lateral incision. Landmarks accessible through the medial or lateral incision are additionally used to align the cutting guide with the distal femur. The tibial cutting guide is aligned using a standard extra-medullary alignment system but with the tibial guide in a medial or lateral position to the proximal tibia to allow access to the tibia through the medial or lateral incision.

Further objects, features, and advantages of the present invention over the prior art will become apparent from the detailed description of the drawings which follows, when considered with the attached figures.

DESCRIPTION OF THE DRAWINGS

FIG. 2 is a side view of a patient's leg illustrating the relative location of a medially or laterally located incision used to access the knee for total knee replacement in accordance with the present invention;

FIG. 3 illustrates the leg of FIG. 2 with the incision thereof opened to provide access to the knee joint;

FIG. 4 illustrates a femoral cutting guide for use in resecting the distal end of the femur for accepting a replacement femoral knee component;

FIG. 5 illustrates a tibial cutting guide for use in resecting the proximal end of the tibia for accepting a replacement tibial knee component;

FIG. 10A is a perspective view of a femoral component of a posterior cruciate ligament retaining design;

FIG. 10B is a perspective view of a femoral component of a posterior cruciate ligament substituting design;

FIG. 11A is a plan view of a tibial component for use with the femoral component illustrated in FIG. 10A;

FIG. 11B is a plan view of a tibial component for use with the femoral component illustrated in FIG. 10B;

FIG. 12A is a perspective view of the tibial component illustrated in FIG. 11A;

FIG. 12B is a perspective view of the tibial component illustrated in FIG. 11B;

DETAILED DESCRIPTION OF THE INVENTION

Figure 1A:
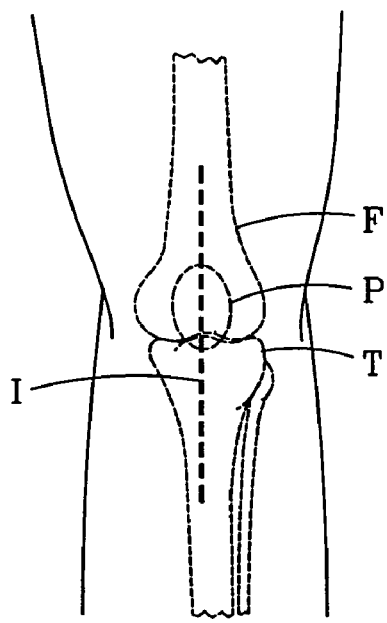
FIG. 1A is a front or anterior view of a portion of a human patient's leg illustrating the relative location and size of an incision used to access the knee for total knee replacement in accordance with the prior art.
Figure 1B:
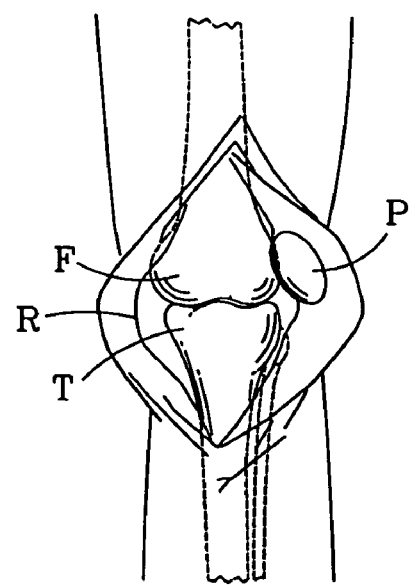
FIG. 1B illustrates the knee of FIG. 1A with a patella and extensor mechanism of the knee displaced and everted, exposing the femur and tibia of the leg in accordance with the method of total knee replacement of the prior art.
Figure 1C:
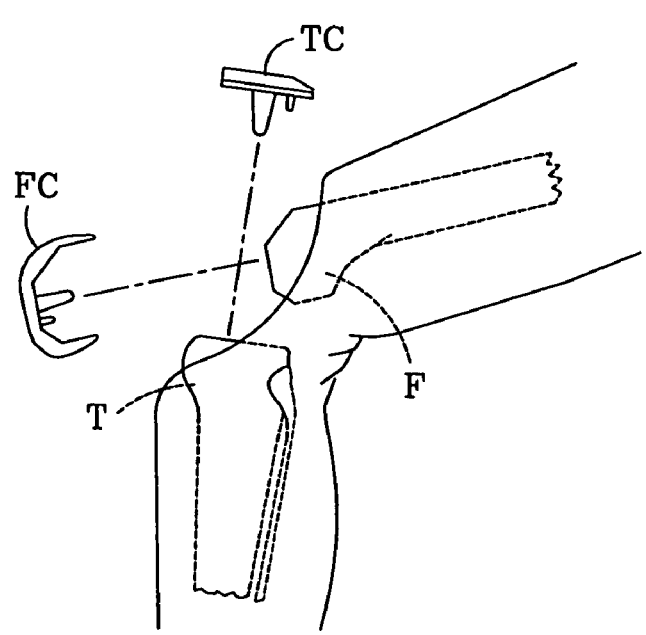
FIG. 1C is a side view of the knee wherein the femur and tibia have been resected and replacement knee components are oriented for installation in accordance with the method of total knee replacement of the prior art.
Figure 1D:
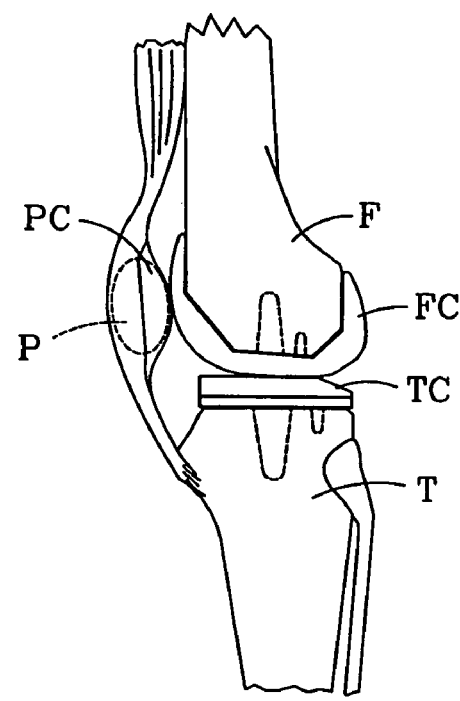
FIG. 1D illustrates a replacement knee in accordance with the prior art, the replacement knee including a femoral component affixed to the resected femur, a tibial component affixed to the resected tibia, and a patellar component affixed to the resected patella.

The invention is a method and apparatus for total knee arthroplasty. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One embodiment of the invention is a method for total knee replacement which is minimally invasive. Referring to FIG. 2, in accordance with the method, an incision I is made either generally medially or laterally along the mid-lateral line of the knee. By "generally" medially or laterally, it is contemplated that the incision I may be somewhat anterior or posterior to the mid-lateral line. So located, the incision I is generally centered over the tibio-femoral or "knee" joint. In a preferred embodiment, the incision I is about 8-12 centimeters long.

Several factors may be considered in determining whether the incision I should be located medially or laterally to the knee. The choice of exact incision location may depend upon any pre-operative deformity to be corrected. Generally, the ligaments on the concave side of the deformity are contracted requiring release. In this instance, the incision I should be made on the concave side of the deformity to allow for appropriate ligament balancing. The deep incision may divide ligament structures such as the medial collateral ligament or iliotibial band along the length of its fibers, but in general does not release the ligaments transversely unless for ligament balancing. The incision may be best made along the mid-lateral line on the medial or lateral side of the knee, or somewhat anterior or posterior to the mid-lateral line depending on location of crucial ligamentous structures.

Referring to FIG. 3, access is provided to the knee joint through the incision I. One or more retractors or other devices may be used to spread or open the incision I. Notably, access is provided to the knee joint without the need to evert the patella P. In a preferred embodiment, the patellar retinaculum is incised along the length of the incision in order to provide greater access to the knee joint, but again, the patella P is not everted. Ligaments are released or elongated to allow appropriate balancing and correction of deformity in accordance with the standard practice of total knee replacement surgery.

A number of actions may be taken to provide access to and prepare the knee joint area for bony resection and affixation of the replacement knee components. In one embodiment, synovium may be excised, as may be a portion of the infrapatellar fat pad or body. The menisci and one or both cruciate ligaments may be excised as is done in a standard total knee replacement.

The proximal end of the tibia T and the distal end of the femur F are then resected to accommodate the replacement knee components. In accordance with the method, access for resection is provided through the medial or laterally located incision I. Notably, unlike in the prior art, anterior displacement or dislocation of the tibia from the femur is not necessary to adequately expose the proximal tibia.

Referring generally to FIG. 4, in one embodiment, a femoral cutting guide 20 is located exterior to the patient's femur adjacent the incision I. A cutting apparatus is then used to resect the distal end of the femur F. Greater details regarding the femoral cutting guide 20 and a method of using an embodiment of the femoral cutting guide 20 of the invention are detailed below.

Referring generally to FIG. 5, in one embodiment, a tibial cutting guide 22 is located exterior to the patient's tibia adjacent the incision I. A cutting apparatus is then used to resect the proximal end of the tibia T. Greater details regarding the tibial cutting guide 22 and method of using an embodiment of the tibial cutting guide 22 of the invention are detailed below.

Figure 6:
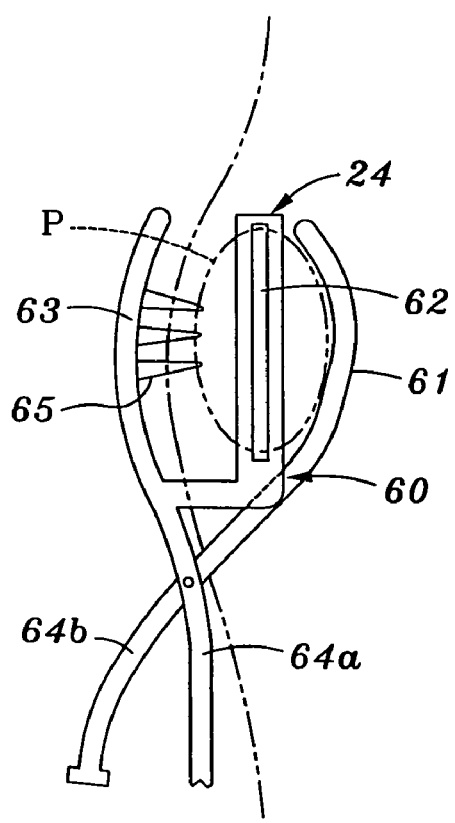
FIG. 6 illustrates a patellar cutting guide for use in resecting the patella for accepting a replacement patellar knee component.

Referring generally to FIG. 6, in one embodiment, the patella P may be resected as well. A patellar cutting guide 24 may be used for this purpose.

Figure 7:
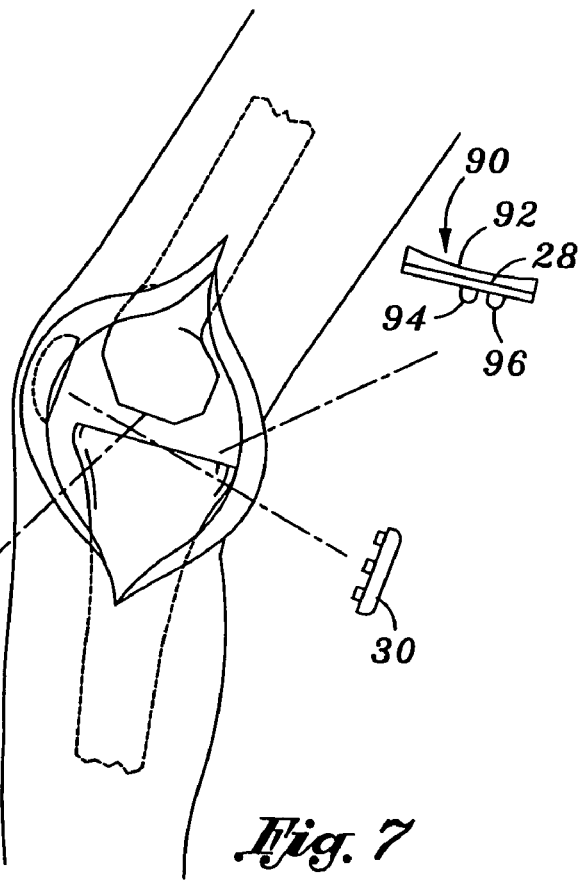
FIG. 7 illustrates a replacement femoral knee component, replacement tibial knee component, and replacement patellar knee component of the invention for connection to a resected femur, tibia and patella, respectively.

Referring to FIG. 7, replacement knee components are then implanted to re-surface the knee joint. As illustrated, the replacement knee components include a femoral component 26 and a tibial component 28. The replacement knee components may also include a patellar component 30. Details regarding embodiments of these components are set forth below.

The components may be connected to the femur F, tibia T and patella P, respectively, in a variety of manners known in the art. In a preferred embodiment, the components include one or more short pegs, stems or other extensions for engagement with passages or recesses in the bone. Cement is the primary means for affixing the components to the bone, although screws and/or bone in-growth into a porous surface on the under surfaces of the components may also be utilized.

Figure 8:
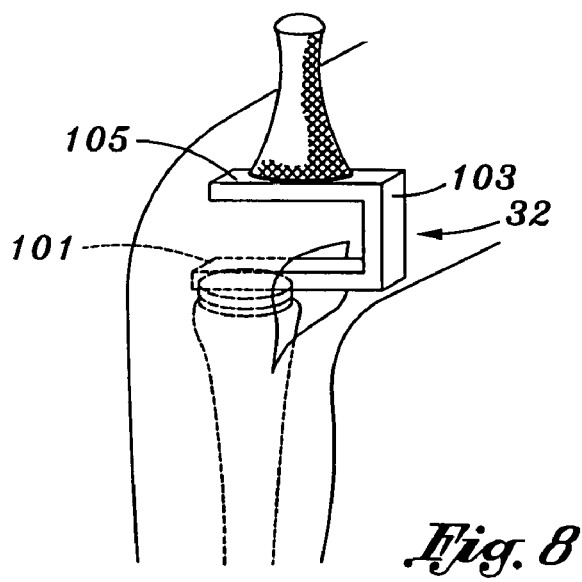
FIG. 8 illustrates an impactor for use in placing one or more of the replacement knee components of the invention, including the tibial component.

Referring to FIG. 8, in one embodiment an impactor 32 may be used to affix the tibial component 28 to the tibia T and the femoral component 26 to the femur F. The impactor 32 is utilized to drive the femoral component 26 onto the distal end of the femur F and the tibial component 28 onto the proximal end of the tibia T. A clamp may be used to compress the patellar component to the patella.

One or more embodiments of the invention comprise apparatus for total knee arthroplasty, including total knee replacement components and devices for preparing the bones and affixing the components to the bones. This apparatus and additional details of the method of the invention will now be described.

As described above, in one step of a method of the invention, the distal end of the femur F is resected for fitting with the femoral knee component 26. In one embodiment, the femoral cutting guide 20 is one apparatus provided for this purpose. In general, the femoral cutting guide 20 is designed to permit resection of the femur F through the medial or lateral incision I. Thus, unlike the anterior access of the prior art, in this embodiment the femoral cutting guide 20 must be designed for resecting the femur F where access is provided through only a small medial or lateral incision I without the need for eversion of the patella.

To this end, in one embodiment, the femoral cutting guide 20 is arranged to be located exterior to the femur of the patient on the medial or lateral side of the distal femur. As illustrated, the femoral cutting guide 20 includes a body 40 having a slot or guideway 42 formed therein. In one embodiment, the body 40 is generally flat and plate-like.

The slot or guideway 42 is useful in guiding a cutting implement, such as a reciprocating or oscillating saw or rotating milling device. As described below, such a cutting implement in one embodiment is extended through the slot 42 generally perpendicular to the body 40.

As illustrated, in one embodiment, the slot or guideway 42 is generally "U"-shaped. A first portion 42a of the slot 42 is arranged for resecting the anterior portion of the distal femur F and extends generally parallel to the longitudinal axis of the femur. A second portion 42b of the slot 42 is arranged for resecting the distal end of the femur F and extends generally perpendicular to the longitudinal axis of the femur. A third portion 42c of the slot 42 is arranged for resecting the posterior distal end of the femur F and extends generally parallel to the longitudinal axis of the femur. Additional slots 42d, 42e may be arranged for angled resection of additional bone from the distal femur.

It will be appreciated that in this arrangement, resection occurs generally perpendicular to a plane extending in the anterior-posterior direction through the knee joint, including the femur F. Using the femoral cutting guide 20, the anterior portion of the distal femur F, the posterior portion of the distal femur F including the lateral and medial condyles thereof, and the distal end of the femur F are all resected. The knee may be flexed or extended for each cut to move ligaments and neurovascular structure out the way to cause the least chance of injury to these structures. Retractors or soft tissue protectors may be inserted through the medial or lateral incision to protect ligaments and neurovascular structures during cutting.

The femoral cutting guide 20 may be securely located in a variety of manners. In one embodiment, the femoral cutting guide 20 is connected to the distal femur with pins, screws or the like. The femoral cutting guide 20 is preferably securable in one or more fixed positions, or may be adjustable once connected to the distal femur, to ensure proper alignment for resecting the distal femur. As described below, a variety of methods and apparatus may be utilized to properly align the femoral cutting guide 20 before cutting.

The slot or guide 42 may have other shapes than illustrated, depending upon the particular resected femur profile desired. In one or more embodiments, the thickness of the body 40 may be varied to serve as a cutting depth limiter for the cutting tool. Additionally, the body 40 must be thick enough to stabilize the cutting instrument being passed through the slot 42 such that tilting of the cutting instrument and resultant over or under resecting does not occur.

The femoral cutting guide 20 may be constructed of a variety of materials. In a preferred embodiment, the femoral cutting guide 20 is constructed from an inert, durable and sterilizable material, such as cobalt chrome, stainless steel or ceramic.

As described above, in one step of a method of the invention, the proximal end of the tibia T is resected for fitting with the tibial knee component 28. In one embodiment, the tibial cutting guide 22 is one apparatus provided for this purpose. In general, the tibial cutting guide 22 is designed to permit resecting of the tibia T through the medial or lateral incision I. Thus, unlike the anterior access of the prior art, in this embodiment the tibial cutting guide 22 must be designed for resecting of the tibia T where access is provided through only a small medial or lateral incision I. Anterior displacement or dislocation of the tibia from the femur is not required using this technique.

To this end, in one embodiment, the tibial cutting guide 22 is arranged to be located exterior to the tibia of the patient on the medial or lateral side of the proximal tibia. As illustrated, the tibial cutting guide 22 includes a body 50. In one embodiment, the body 50 is plate-like in form.

A slot or guideway 52 is formed in or defined by the body 50. The slot or guideway 52 is useful in accepting and guiding a cutting implement, such as a reciprocating or oscillating saw or other milling device. As with the femoral cutting guide 20, as detailed below, such a cutting implement is extended generally perpendicular to the body 50 during cutting.

In the embodiment illustrated, the slot 52 has a generally planar area 52*a* for sectioning the proximal end of the tibia T in a horizontal plane generally 1-7 degrees posteriorly sloped to the longitudinal axis of the tibia T. To aid in locating the cutting implement and to avoid cutting beyond the anterior and posterior portions of the tibia T, first and second vertical stops 52*b,c* are located at either end of the slot 52. Retractors or soft tissue protectors may be inserted through the medial or lateral incision I to protect ligaments and neurovascular structures during cutting. The knee may be flexed or extended in order to protect ligaments and neurovascular structures during different parts of the cut.

As with the femoral cutting guide 20, the tibial cutting guide 22 may be securely positioned in a variety of manners. Secure fixation to the tibia may be achieved with pins or screws. One particular method of securing the tibial cutting guide 22 is described in detail below in conjunction with FIGS. 14A and 14B. The tibial cutting guide 22 may also be constructed in a wide variety of manners other than that illustrated. For example, the shape of the slot 52 may vary depending upon the desired resected tibial profile.

The tibial cutting guide 22 is preferably also constructed of a variety of materials, and preferably an inert, durable and sterilizable material such as cobalt chrome, stainless steel or ceramic.

As described above, in one step of a method of the invention, the posterior portion of the patella P may be resected for implanting with the patellar knee component 30. In one embodiment, the patellar cutting guide 24 is one apparatus provided for this purpose. In general, the patellar cutting guide 24 is designed to permit resecting of the patella P through the lateral or medial incision I. Thus, unlike the anterior access of the prior art, in this embodiment the patellar cutting guide 24 must be designed for resecting the patella P where access is provided through only a small lateral or medial incision I. Eversion of the patella is not required. Disection of the overlying skin, subcutaneous tissues and bursa is also not required.

To this end, in one embodiment, the patellar cutting guide 24 includes a means for guiding a cutting implement, the means for guiding being position adjustable so that the depth of cut may be selected, and a means for retaining or holding the patella during cutting. In one arrangement, the means for retaining includes a means for penetrating the skin and subcutaneous tissues and engaging the anterior of the patella, and a means extending through said medial or lateral incision for engaging the posterior of the patella.

In one embodiment, the patellar cutting guide 24 is arranged as a clamp that is affixed to the anterior and posterior surfaces of the patella. The patellar cutting guide 24 also defines a slot for guiding a cutting implement. In one embodiment, the patellar cutting guide 24 has two parts. The first part comprises a body 60 which is arranged to be located exterior to the knee. The body 60 defines a slot or guideway 62. The slot or guideway 62 is useful in guiding a cutting implement, such as a reciprocating or oscillating saw or other milling device. In one embodiment, the body 60 defines a generally elongate slot.

The body 60 also includes an arm or clamp 63. The arm or clamp 63 is arranged to extend along the exterior of the anterior of the knee patella P when the portion of the body 60 defining the slot 62 is aligned with the medial or lateral incision I. It will thus be appreciated that the portion of the body 60 defining the slot 62 and the arm 63 do not lie in the same plane, horizontally or vertically.

Preferably, one or more spikes 65 extend from the arm 63. The spikes 65 are preferably sharp, skin penetrating elements, designed to pass through the skin and subcutaneous tissues and engage the patella P.

The patellar cutting guide 24 also includes a stop 61. The stop 61 is designed to extend into the medial or lateral incision I and engage the posterior of the patella P. In one embodiment, the stop 61 includes a cupped or curved portion adapted to engage the posterior of the patella P. In that at least a portion of the stop 61 is configured to be located at the posterior of the patella P while the portion of the body 60 defining the slot 62 is located exterior to the knee, it will be appreciated that these portions do not lie in the same plane. However, in that the clamp 63 is configured to engage the anterior of the patella while a portion of the stop 61 engages the posterior of the patella, the clamp 63 and that portion of the stop may generally lie in the same plane. As illustrated, the portion of the stop 61 and the portion of the arm or clamp 63 which are designed to be located adjacent the patella P may be curved or cupped to define a space there between in which the patella P, tissue and the like may be located.

In a preferred embodiment, the stop 61 and the body 60 are hingedly connected, permitting them to be moved with respect to one another. As illustrated, the stop 61 and the body 60 include lever arms 64a,b located on opposing sites of a hinge. These lever arms 64a,b may be used to manipulate the relative position of the body 60 and stop 61. Preferably, the lever arms 64a,b are used to compress the patella P between the stop 61 and the arm 63, securely retaining it in a fixed position while the patella is resected. In general, the patellar cutting guide 24 is positioned so that the cutting implement, when located in the slot 62, removes the posterior articular surface of the patella P generally parallel to the anterior surface of the patella and at a specified constant depth.

The patellar cutting guide 24 may also be constructed in a wide variety of manners other than that illustrated. For example, the slot 62 may have a variety of shapes or sizes, as may the body 60 and arm 63. For example, the portion of the body 60 defining the slot 62 may be adjustable in position relative to the arm 63. In this manner, once the patella P is fixed between the arm 63 and the stop 61, the location of the slot 62 may be adjusted so that the patella P is resected at the exact depth required or desired. For example, the slot 62 may be defined by a guide member which extends through a passage in the arm 63 and which can be fixed in a variety of positions with the set screw or the like.

It will also be appreciated that the relative position of the stop 61 and the body 60 may be adjustable by other than a hinged connection. For example, a rachet-slide or other moving connection may be used. The patellar cutting guide 24 may comprise individual elements which may or may not be connectable (e.g. separate body defining a slot, arm or stop.) One or more spikes 65 may be used. Further, elements other than spikes as illustrated may be used to engage the anterior of the patella P.

In a preferred embodiment of the invention, means are provided for determining the relative positions of the guides, instruments, and components during the procedure. In one embodiment, the means comprises an image or computer assisted/guided system, which systems in and of themselves are well known in the prior art and which systems per se do not form the invention herein.

One embodiment of an image guided system is illustrated and will be described herein. It will be understood that the system illustrated and described is for reference only and a wide variety of other systems may be utilized. These systems are often referred to under the term IGS for "image guided surgery." In general, these systems generally employ at least one sensor, at least two detectors, and a computer assisted guidance system. An image of a portion of a patient's body is displayed. Position information provided by the sensor and detectors is correlated to the image, providing the viewer with a variety of information. The system may be used to provide spacial position information, for example, of a surgeon's instruments relative to a portion of a patient's anatomy, or the relative positions of different portions of a patient's anatomy.

These systems may have a variety of configurations. As indicated in greater detail below, the system may be arranged to accept a base image in a variety of forms. For example, the system may be arranged to accept and display an image of a portion of a patient's anatomy obtained by plain x-ray, fluoroscopy, magnetic resonance (MRI), computed topographic (CT) or other techniques. The sensors which are used to gain position information which may be correlated to the image may be active or passive. The position of passive sensors is generally obtained by detectors external to the sensor, such as by using a beam of light bounced off of the sensor. The position of an active sensor is generally obtained by data transmitted or provided by the sensor itself to the detectors. These sensors may be of a variety of configurations, depending on the particular system. Some sensors require a direct line of sight between the sensor and the detectors, while others do not. Of course, other systems now being developed or developed in the future may also be utilized.

In one embodiment, at least one position sensor is associated with each bone and the cutting guide, instrument, resecting tools, or other components. The position sensors are utilized to generate position information for use with the cutting guide, instrument, resecting tools or component placement.

Illustrated in FIG. 4 is one arrangement of an image guidance tracking system for reference in understanding a method of the invention. In this embodiment, a position sensor 77 is connected to the femur F. In addition, a component sensor 74 is connected to the femoral cutting guide 20.

In one embodiment of the invention, patient image data is obtained. As indicated above, depending upon the system utilized, this image data may be obtained using plain x-ray, fluoroscopy, magnetic resonance imaging (MRI), computed tomograph (CT) or other techniques. Image data is obtained regarding the patient's knee, including the femur, tibia and patella. These images are loaded onto a computer workstation which includes a visible display device. In another embodiment, the knee is represented visually by a 3-dimensional depiction, such as a drawing, the dimensions of which are fed into the computer by direct measurement from the patient's anatomy.

The position sensors are utilized to determine the position of the patient's actual bony anatomy, the cutting guides, instruments, cutting tools, components or other tools. The actual position data is calibrated or compared against and illustrated on one of the patient images. In this manner, the physician is able to view the display and determine the true position of the components in relation to the patient's anatomy. This is particularly useful where the internal anatomy of the knee cannot be fully visualized or the visual alignment landmarks, such as the tibial and femoral intramedullary canals, cannot be accessed.

In the embodiment illustrated, the position sensor 77 is utilized to determine the position of the patient's femur F, which position is then calibrated against the actual image data of the patient's femur F. Then, the position sensor 74 is utilized to determine the actual position of the femoral cutting guide 20. This information is calibrated against the femur position and illustrated in relative spacial position on the display. The surgeon may then determine, by viewing the display, that the femoral cutting guide 20 is correctly positioned. The cutting tool is then placed through the guide, and its position can be tracked, as well, by using the display.

Referring to FIG. 5, similar sensors 76,78 may be used to determine the position of the tibial cutting guide 22 relative to the tibia. Likewise, though not shown, similar sensors may be utilized to determine the location of the patellar cutting guide 24. Also, such sensors may be connected to trial femoral, tibial and patellar knee components before insertion of the final femoral knee component 26, tibial knee component 28, and patellar knee component 30. Sensors may also be connected to the impactor 32 or other instruments/components/tools.

These image assisting components are useful in providing the surgeon with information which is otherwise limited due to the use of such a small incision. In the prior art, the entire knee is widely exposed from the anterior approach and thus is entirely visible, and critical landmarks such as the femoral and tibial intramedullary canals, the femoral condyles, femoral epicondyles, and the tibial tubercle are easily accessible. In the method of the invention, however, the size of the incision is minimized. In order to keep the incision as small as possible, but still ensure proper resecting, alignment and component placement, the image guided system is preferably utilized. The image assistance is useful, for example, in ensuring proper depth of resection in the side opposite the incision (as a line of sight is not available through the knee from the incision I to the opposite side).

As indicated, the method of the invention may also be performed without the above-referenced image guidance assistance. In accordance with one embodiment of the invention, various apparatus are provided for use in a method of placing the components.

Figure 13A:
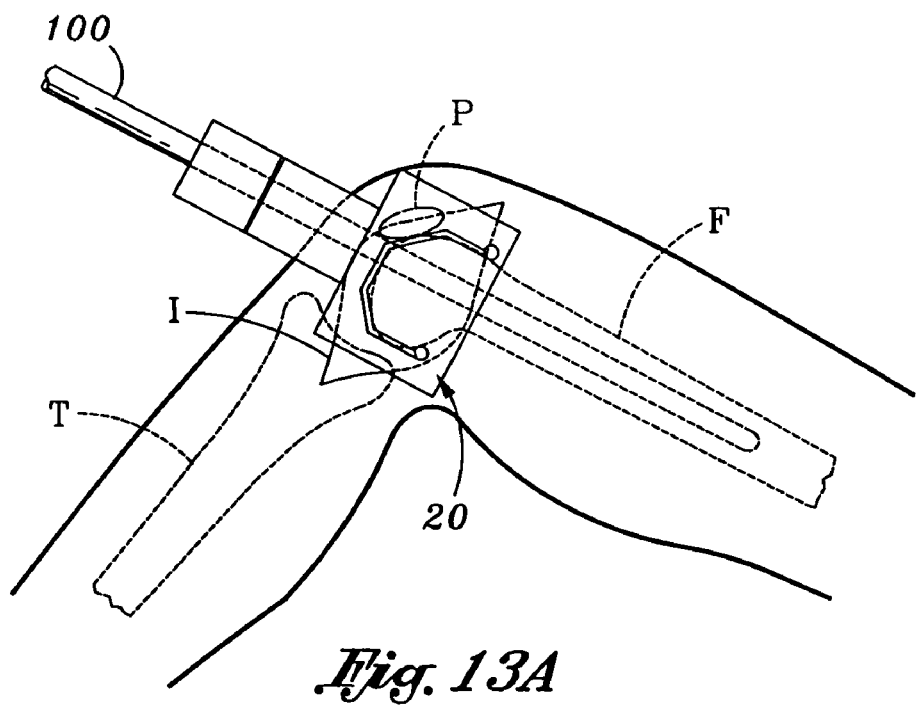
FIG. 13A is a side view of a knee illustrating a femoral intra-medullary rod passing through a small anterior incision and the patellar tendon into the femoral canal, and further illustrating an arm connected to the rod for supporting a femoral cutting guide in an aligned resecting position.
Figure 13B:
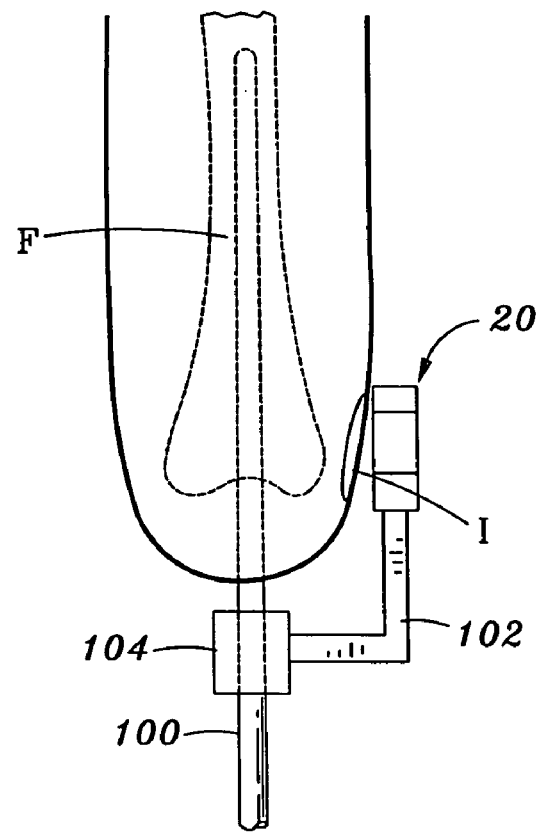
FIG. 13B is a front view of the knee, rod, arm and cutting guide illustrated in FIG. 13A.

Referring to FIGS. 13A and 13B, in one embodiment of the invention, an intramedullary rod 100 is passed through a small anterior incision and through the patellar tendon into the intramedullary canal of the femur F. In one embodiment, the anterior incision is generally 1 cm long or less. The patellar tendon is incised in line with its fibers just distal to the patella P to permit passage of the rod 100.

The femoral cutting guide, such as the femoral cutting guide 20 described above and illustrated in FIG. 4, is attached to the intramedullary rod 100 to align the femoral cutting guide with the distal femur through the medial or lateral incision I. In one embodiment, as illustrated, the femoral cutting guide is connected to the intramedullary rod 100 using an arm 102. As illustrated, a first end or portion of the arm 102 is arranged to be selectively connected to the rod 100. Preferably, the position of the arm 102 relative to the rod 100 can be adjusted. As illustrated, the first end of the arm 102 includes a sleeve 104 which accepts the rod 100, permitting the first end of the arm 102 to be moved along the rod 100 and be rotated about the rod 100. One or more set screws or the like (not shown) may be used to secure the arm 102 to the rod 100 in a fixed position.

The femoral cutting guide is connected to the second end of the arm 102. As illustrated, the arm 102 is configured so that when connected, the femoral cutting guide is located along the side of the knee in alignment with the lateral or medial incision I. In the embodiment illustrated, the arm 102 is "L"-shaped having a first portion which extends outwardly from the rod 100 and a second portion extending generally parallel to the rod 100. The femoral cutting guide may be connected to the second end of the arm 102 in a variety of manners, including by permanent connection, mating threads and other means.

In accordance with the invention, the femoral cutting guide is placed in position adjacent the distal femur along the medial or lateral incision I. Utilizing landmarks which are accessible through the small medial or lateral incision I, such as the anterior shaft of the femur F, the condyles or epicondyles, the femoral cutting guide is further aligned and then attached to the medial or lateral distal femur using pins, screws or the like. A cutting instrument is then passed through the guide to resect the distal femur F, as described above.

Figure 14A:
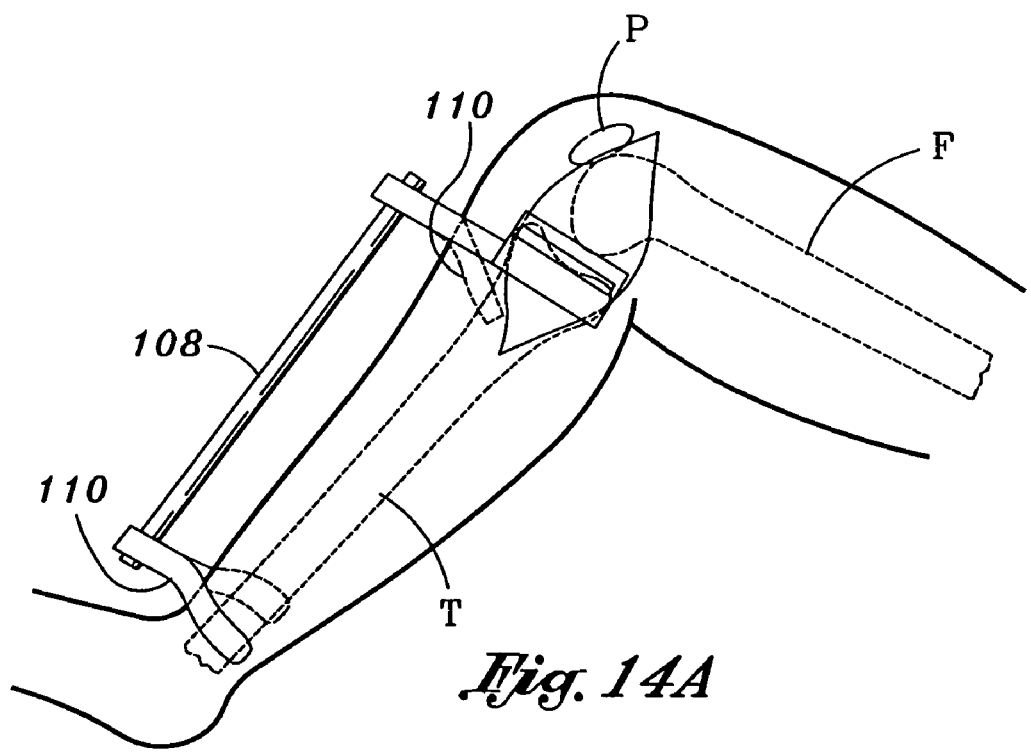
FIG. 14A is a side view of a knee illustrating a tibial cutting guide attached to an extra-medullary alignment guide in an aligned resecting position.
Figure 14B:
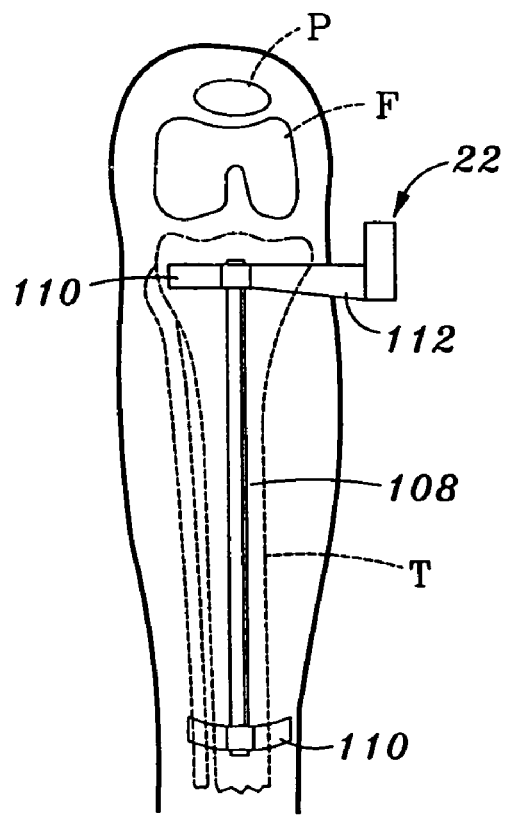
FIG. 14B is a front view of the knee, alignment guide and cutting guide illustrated in FIG. 14A.

Referring to FIGS. 14A and 14B, an extra-medullary alignment guide 108 is provided for aligning a tibial cutting guide, such as the tibial cutting guide 22 described above and illustrated in FIG. 5. As illustrated, the extra-medullary alignment guide 108 comprises an elongate member having a first end and a second end. At each end, a clamp 110 is provided. As illustrated, each clamp 110 comprises a generally "C" or "V" shaped member for extension about the exterior of the leg of a patient. These clamps 110 provide support for the elongate central portion of the guide 108. Of course, the alignment guide 108 may have a variety of other configurations.

The tibial cutting guide is connected to the extra-medullary alignment guide 108, such as with an arm 12. Once again, means of connection may be provided permitting the position of the arm 112, and thus a connected cutting guide, to be moved relative to the alignment guide 108 for alignment purposes. The tibial cutting guide may also be connected to the arm 112 in a variety of manners, including by means permitting the tibial cutting guide to be disconnected from the arm 112.

Once the arm 112 and tibial cutting guide are connected to one another and the extra-medullary alignment guide 108, the tibial cutting guide is aligned along the medial or lateral proximal tibia with the coronal and sagittal planes. The tibial cutting guide can then be securely connected to the tibia through the medial or lateral incision, such as with pins, screws or the like as described above. A cutting instrument may then be used to resect the proximal tibia as guided by the tibial cutting guide.

In accordance with this apparatus and the above-described methods, the femoral and tibial cutting guides are aligned using available anatomic landmarks utilizing instrumentation that is specifically adapted to allow access of the femoral intra-medullary canal and other anatomical landmarks without use of a large incision, eversion of the patella, or anterior displacement of the tibia from the femur. Cutting guides and alignment instruments are modified to be attached to the distal femur and proximal tibia through a small medial or lateral incision, with the addition of a much smaller accessory anterior incision for placement of the femoral intra-medullary rod. Additional instruments for positioning of the cutting guides are modified for use through the small medial or lateral incision. In general, these instruments are small, compact, and designed to facilitate referencing the anterior, distal, posterior, medial, and lateral femur, and the upper surface of the tibia to allow appropriate positioning and fixation of the cutting guides to the medial or lateral femur and tibia through a very small incision.

In one or more embodiments of the invention, a specially configured femoral component 26, tibial component 28 and patellar component 30 are provided. In general, these components are specially designed to both act as total knee replacement components, and are also adapted to be positioned through the miniature medial or lateral incision I.

Referring to FIG. 7, in one embodiment, the femoral component 26 comprises a body 80 having an inner surface 82 and outer surface 84. As described below, when the femoral component 26 is connected to the femur F, the inner surface 82 is directed against the femur F. The outer surface 84 is located for contact against a mating surface of the tibial component 28 and patellar component 30. As illustrated, the femoral component 26 is generally "C"-shaped, with the inner surface 82 having the shape of a trough.

Figure 9A:
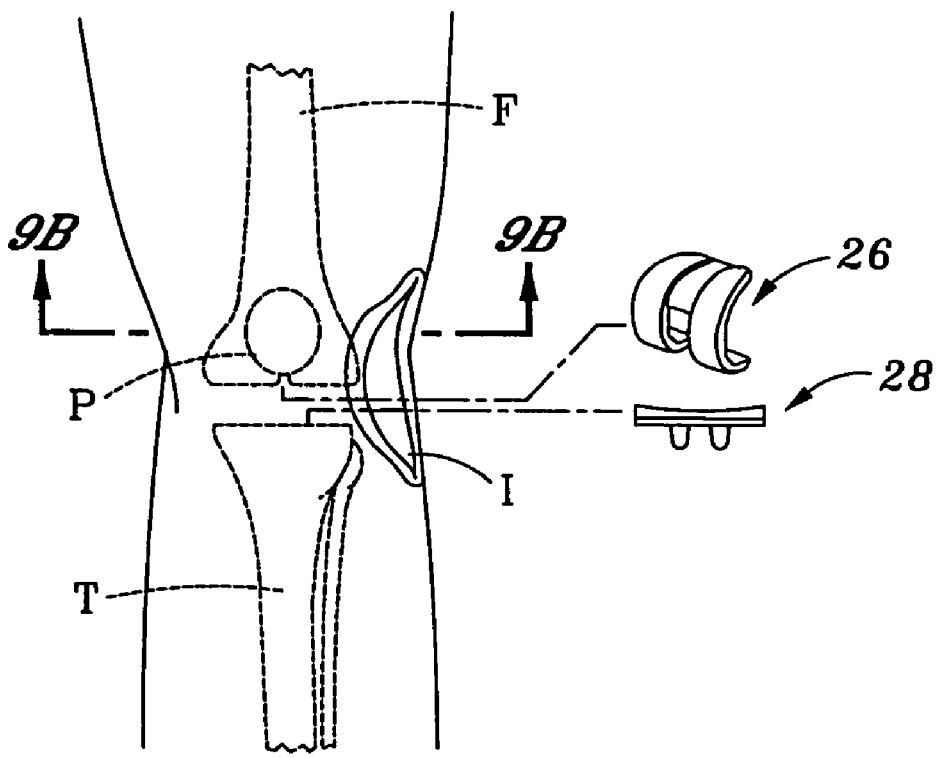
FIG. 9A is a front or anterior view of the knee of FIG. 7 illustrating a femoral and tibial knee component oriented for insertion through a lateral incision in accordance with the invention.

One or more fixation pegs 86 extend from the inner surface 82. The pegs 86 are preferably very short in dimension. In one embodiment, the pegs 86 are no longer than about 5-10 mm long. In another embodiment of the invention, the femoral component 26 does not include the pegs. In general, it is desired that the pegs 86 be short or non-existent. The pegs 86 may have a variety of shapes and configurations, but are preferably generally circular in cross-sectional shape. This arrangement permits the surgeon to align the "trough" shaped inner surface 82 with the femur F from the medial or lateral side, and extend it transversely through the incision I into engagement with the femur F, as illustrated in FIG. 9A. Minimizing the length of the pegs 86 minimizes the distance that the femoral component 26 must be offset downwardly along the axis of the femur F from the distal end of the femur F in order to locate the femoral component 26 at the distal end of the femur F. Once positioned in the correct medial-lateral position, the femoral component is driven into the distal end of the femur F utilizing the impactor 32.

The femoral component may be of a posterior cruciate ligament retaining design or of a posterior cruciate substituting design, as illustrated in FIGS. 10A and 10B, and as is well known in the prior art. FIG. 10A illustrates a femoral component 26A without pegs of a posterior cruciate ligament retaining design. This femoral component 26A is generally "C"-shaped, and has a generally upwardly extending anterior portion 110A and a generally upstanding posterior portion 112A, with a trough 114A located there between. The femoral component 26A has an inner surface 116A and an outer surface 118A. The inner surface 116A is for mating to a resected femur. The outer surface 118A is for abutting a tibial component. As illustrated, the posterior portion 112A comprises a pair of separated medial and lateral condyle portions 120A, 122A.

Advantageously, the femoral component 26A has a low profile in the lateral or transverse (i.e. in a direction aligned with the trough) direction. In other words, the maximum distance between the inner and outer surfaces 116A, 118A, especially in the area of the trough, is relatively small. In this manner, the femoral component 26A may be aligned laterally with the femur (as illustrated in FIG. 7), and inserted through the medial or lateral incision I and placed onto the femur F with little displacement of the femur relative to the tibia.

FIG. 10B illustrates a femoral component 26B of a posterior cruciate substituting design. This embodiment component has a cam 27B between the posterior aspect of the medial and lateral condyle portions to contact a post 35B on a complimentary tibial insert (see FIG. 11B). Preferably, the cam 27B has a low profile and does not extend upwardly beyond the upper or inner surface of the condyle portions, again contributing to a low profile and minimizing interference during lateral insertion and alignment of the component 26B with the femur.

In this design, the cam 27B cooperates with the post 35B of the tibial component 28B to prevent posterior sublutation of the tibia on the femur with knee flexion. Notably, this style of posteriorly stabilized femoral component 26B has a low profile, with no inset box or walls extending upwardly from the inner surface, unlike that found with other posteriorly stabilized components.

Referring again to FIG. 7, in one embodiment, the tibial component 28 also comprises a body 90. As is known, the tibial component 28 has an insert 92, such as made of plastic which forms the mating surface for the outer surface of the femoral component 26.

In one embodiment, one or more pegs 94,96 extend from the under side of the tibial component 28 opposite the insert 92. The pegs 94,96 are preferably of a very short dimension, preferably being no more than about 5-10 mm long. The pegs 94,96 may be of a variety of shapes and configurations. In one embodiment, the pegs 94,96 have a generally circular cross-sectional shape. Once again, the pegs 94,96 of the tibial component 28 are minimized for the same reasons that the pegs 86 of the femoral component 26 are also minimized. This arrangement allows the tibial component to be inserted transversely over the proximal tibia through the medial or lateral incision and then onto the surface of the tibia using the impactor 32, as illustrated in FIG. 9A.

In one embodiment, the tibial component 28 comprises a base for affixing to the tibia, and an insert which is affixed to the base and comprises the surface which engages the femoral component. In one embodiment, the base is constructed of cobalt chrome, titanium or ceramic and the insert of high density polyethylene.

The tibial component may be of a symmetric or asymmetric design with respect to the medial and lateral aspects. The polyethylene insert is designed to mate tightly with the tibial component using a dovetail mechanism. The polyethylene insert is designed for insertion into the base from the medial or lateral side. A locking mechanism such as a step on the medial and lateral sides of the base allow secure locking of the polyethylene insert into the tibial component when fully inserted.

FIGS. 11A and 12A illustrate in detail one embodiment of a tibial component 28A including a base 31A and insert 33A. This embodiment tibial component 28A is partially suited for use with the femoral component 26A illustrated in FIG. 10A. As illustrated, the base 31A and insert 33A have a mating pin and groove or "dovetail" configuration. The base 31A and insert 33A both have anterior 125A and posterior 127A portions, and opposing sides located between the anterior and posterior portions 125A,127A. A slight depression is formed in a top surface of the insert 33A between the anterior and posterior portions 125A, 127A, formatting with the outer surface of a femoral component.

A groove 126A is formed in the top of the base 31A and extends in a lateral (i.e. side to side) direction. Likewise, a mating pin 128A is defined by the lower surface of the insert 33A, the pin 128A extending in a lateral direction, permitting alignment and insertion of the insert 33A through the medial or lateral incision I into the groove 126A of the base 31A.

The pin 128A and groove 126A may be formed in a variety of fashions. As illustrated, the pin 128A comprises a downwardly extending area of the bottom of the insert 33A. In the embodiment illustrated, the groove 126A defines a pair of overhanging ledges 130A for mating with a pair of extensions 132A of the pin 128A. The ledges 130A and extensions 132A engage, permitting lateral movement of the insert 33A relative to the base 31A for insertion, but preventing front to back or upward movement of the insert 33A relative to the base 31A. Other mating configurations may be utilized, but preferably, such configurations permit the lateral insertion and alignment of the components as described.

FIGS. 11B and 12B illustrate an embodiment of a tibial component 28B which includes a post 35B in the center of the polyethylene insert which is arranged to mate with the femoral cam of a posterior cruciate ligament substituting femoral component as illustrated in FIG. 10B.

The patellar component 30 may have a variety of configurations including those already known. Once positioned against the cut surface of the patella, it is held with a compression clamp while the bone cement hardens or to press fit against the patella P.

One aspect of the invention is one or more tools or devices for use in placing the components. Illustrated in FIG. 8 is one embodiment of an impactor 32 for use in placing the femoral component 26 or tibial component 28. The impactor 32 includes a contact arm 101 and a driving arm 105 connected by a support 103. The general shape of the impactor 32 is generally "U" or "C"-shaped, such that the contact arm 101 may be placed through the medial or lateral incision I and against the femoral or tibial component 26,28, while the driving arm 105 is located outside of the knee. The driving arm 105 may, as illustrated, include an upwardly extending post or driver designed to transmit the force of hammer blows to the contact arm 101.

In one embodiment, the impactor 32 is constructed of a rigid, durable and sterilizable material such as stainless steel. The exact dimensions of the impactor 32 may vary. Preferably, however, the length of the contact arm 101 is sufficient to extend from the support 103 when located outside of the incision I adjacent the patient's leg, to a position over the femoral component 26 placed in position at the femur F or the tibial component 28 placed in position at the tibia T. In addition, the driving arm 105 is also sufficiently long to extend from the opposing end of the support 103 to a point generally above the distal end of the femur F or proximal end of the tibia T adjacent to the patient's leg.

In use, the surgeon locates the femoral component 26 or tibial component 28. The surgeon then locates the driving arm 105 of the impactor 32 against the femoral component 26 or tibial component 28 (or if the tibial component 28 has a base and insert against the base) by extending the contact arm 101 through the incision I. The surgeon may then impact upon the driving arm 105, which force is transmitted through the impactor 32 to the tibial component 28. This force is useful, for example, in pressing the pegs 86 of the femoral component 26 or the pegs 94,96 of the tibial component 28 into bores or recesses formed in the femur F for the tibia T.

Other specialized instruments designed for use through the short medial or lateral incision I may include hooks or "backbiting" curettes to remove bone spurs from the femur and tibia, soft tissue protectors which can be inserted to protect the anterior or posterior soft tissue, and hooked or curved curettes or spatulas to remove excess cement from around the components. Curved osteotomes may be utilized for removal of femoral or tibial bonus spurs. A sizing caliper or depth gauge may be necessary to measure the dimension of any of the three bones for correct sizing of the implant components.

In one or more embodiments, trial components may be used during the method. A trial femoral component, tibial component and/or patellar component may be used before the actual components are permanently placed in order to ensure proper resection of the femur, tibia and patella and ligament balancing. These trial components may be shaped similar to the actual components, but may be made of lightweight metal or plastic. The trial components need not have the same exacting tolerances and the same durability as the actual components.

In one embodiment, one or more sensors may be connected to the trial components. Position information provided by the sensors may be used in the trial placement process to aid in alignment of the actual components and assessment of the ligament tightness.

The method and apparatus of the invention have numerous benefits. In accordance with the invention, a method is provided for total knee arthroplasty in a minimally invasive manner. Access to the knee joint is provided through a short medially or laterally located incision. Due to the medial or lateral location, access is provided to the knee joint through an incision which is much smaller than the size of incision which would be necessary to access the knee joint from the anterior.

The small medial or lateral incision permits full access to the knee joint, including the distal end of the femur and the proximal end of the tibia. Access is provided without the need to evert the patella. Access through the medial or lateral incision is the primary reason for not needing to evert the patella, and at the same time, because the patella need not be everted, the size of the incision which is necessary to provide access is substantially reduced. The medial or lateral incision also does not require anterior displacement or dislocation of the tibia from the femur for preparation of the tibia or insertion of the tibial component.

Figure 9B:
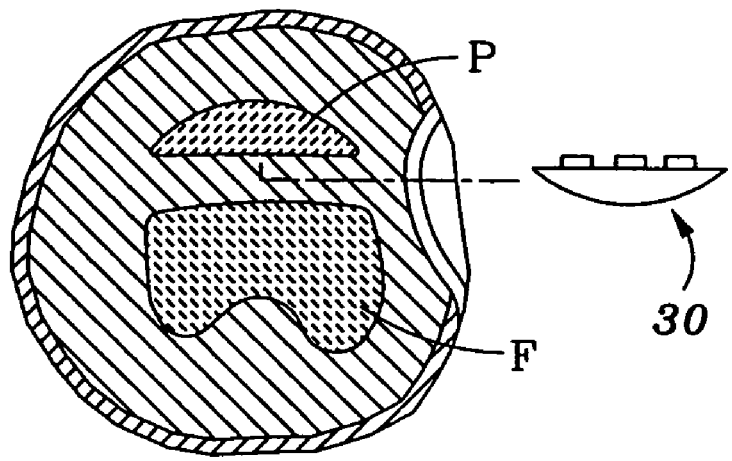
FIG. 9B is a cross-sectional view of the knee illustrated in FIG. 9A taken along line 9B-9B therein, and illustrating a patellar component oriented for insertion through a lateral incision in accordance with the invention.

Access to the knee joint via the medial or lateral incision is also advantageous when considering the resection of the femur, tibia and patella. As illustrated in FIGS. 7 and 9, all of the various planes of resection are accessible from the medial or lateral side of the knee, including the anterior portion of the distal femur F, the distal end of the femur F, the posterior portion of the distal femur F, the proximal end of the tibia T and the patella P.

The greatest advantage realized by the invention is that partial or total knee arthroplasty can be realized with much less trauma to the patient. The trauma to the patient is reduced because the size of the incision is greatly reduced. In addition, the patellar ligament and quadriceps tendon and muscle are not over-extended, stretched, or torn because the patella is not everted. Also, the tibia is not dislocated with resultant potential injury to the knee ligaments and other surrounding structures.

An improved femoral component 26 and tibial component 28 are provided which have aspects of reduced dimensions that allow for a small medial or lateral incision. As indicated, each component 26,28 is designed with short fixation pegs to allow insertion without excessive displacement or dislocation of the joint. The posterior stabilized femoral component has a low profile on the inner surface to facilitate insertion through the medial or lateral incision without excessive displacement of the tibia from the femur or need for a longer incision. Compared to prior art femoral components 26 of the posterior cruciate ligament substituting design, the femoral component 26 has no box or protective side-walls which extend upwardly from the inner surface to surround a mating post of the tibial component. Thus, the femoral component 26 of the invention has a substantially reduced lateral profile relative to prior art components.

The tibial component comprising a base and polyethylene insert are designed such that the insert can be slid into place and locked securely to the base from the medial or lateral side without displacement or dislocation of the joint. These design characteristics allow insertion through a minimized medial or lateral incision.

Additional components are provided for use in preparing the knee joint for accepting the replacement components and placing those components. These components are specially designed to be used in conjunction with a medially or laterally located incision I.

Advantageously, the method of the invention is effectuated through the small medial or lateral incision without the need for access to the intramedullary canals of the femur and tibia, and without the need for clear visualization of common landmarks such as the epicondyles, posterior condylar surfaces, and tibial tubercle.

The cutting guides and implements are arranged to be located or attached along the side of the knee, and not the front, and are further located extra-articular instead of intra-articular. These devices and implements permit preparation of the knee through the small lateral or medial incision and placement of trial and replacement knee components through the lateral or medial incision.

In one configuration, a patellar cutting guide is provided for resecting the patella without dissecting the overlying skin, subcutaneous tissues and bursa from the patella, lessening the chance of skin necrosis from subcutaneous dissection, and lessening the chance of knee tenderness and inability of the patient to kneel after total knee replacement.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A patellar cutting guide for use in resecting a posterior portion of a patella through an incision generally located along the medial or lateral mid-line of a knee, comprising:
   a stop for location posterior to a posterior portion of said patella having a surface configured to abut a posterior portion of said patella, said surface further configured to extend from a distal portion of said posterior portion of said patella to a proximal portion of said posterior portion of said patella when said stop abuts said patella;
   a cutting guide oriented generally perpendicular to said stop, said cutting guide having a generally longitudinal, slot therein for accepting a cutting implement for resecting a posterior portion of said patella;
   a clamp having at least one spike extending therefrom in a direction of said stop, said spike adapted to penetrate the skin and engage an anterior portion of said patella such that said clamp and said stop exert opposite forces posteriorly and anteriorly, respectively; and
   means for moving said clamp relative to said stop, whereby said clamp and stop may be moved into relative positions in which they secure said patella in a fixed position while said cutting implement is utilized to resect said patella.

2. The patellar cutting guide in accordance with claim 1 wherein said means for moving comprises a pivoting connection of said clamp and stop.

3. The patellar cutting guide in accordance with claim 2 wherein said pivoting connection comprises at least one pin, and including a first lever arm extending from a portion of said clamp opposite said pin and a second lever arm extending from a portion of said stop opposite said pin.

4. The patellar cutting guide in accordance with claim 1 wherein said cutting guide is connected to said clamp.

5. A patellar cutting guide for use in resecting a posterior portion of a patella of a knee of a patient, comprising:
   a stop, said stop having a proximal portion and a distal portion, said distal portion configured to be extended through an incision in said knee; and
   a body configured to be located exterior to a knee of a patient, said body defining an elongate slot through which a cutting implement may be passed for resecting a posterior portion of said patella, said body further defining a clamp configured to engage said knee patella at anterior of said patella, said stop and said body movably connected to one another whereby said stop and body may be moved relative to one another and oriented such that when said stop and said body are moved relative to one another, said stop and said body clamp said patella by exerting opposing forces in the posterior-anterior direction of the patella.

6. The patellar cutting guide in accordance with claim 5 wherein said clamp defines a plurality of outwardly extending spikes.

7. The patellar cutting guide in accordance with claim 6 wherein said spikes extend towards said stop.

8. The patellar cutting guide in accordance with claim 5 wherein in said body and said stop are pivotally connected by at least one pin.

9. The patellar cutting guide in accordance with claim 5 wherein said clamp of said body and said stop lie generally in a first plane on at opposing sides of said patella when said cutting guide is in position and said slot is located in a guideway which is located in a second plane which is offset from said first plane.

10. The patellar cutting guide in accordance with claim 5 wherein said slot is defined by a guideway portion of said body.

11. The patellar cutting guide in accordance with claim 5 wherein said clamp and said stop extend outwardly in opposing directions from one another from a point at which said body and stop are connected to one another for relative movement.

12. The patellar cutting guide in accordance with claim 5 wherein said proximal portion of said stop comprises a first lever arm and wherein said body is connected to a second lever arm.

13. A patellar cutting guide for use in resecting the posterior of a patella through a lateral incision in a knee of a patient, the lateral incision thereby defining the boundary between an anterior portion of the knee and an exterior portion of the knee comprising:
   a clamp configured to engage said exterior portion of said knee overlying anterior portion of said patella;
   a stop having a proximal portion and a distal portion, said proximal portion configured to pass through said lateral incision and engage a posterior portion of said patella while said proximal portion remains exterior to said knee; and
   a cutting guide, said cutting guide offset laterally and posteriorly from said clamp, said cutting guide defining a cutting slot, said slot aligned with along said lateral incision when said clamp and stop engage said patella.

14. The patellar cutting guide in accordance with claim 13 including one or more spikes extending from said clamp for passage through tissue overlying said anterior portion of said patella and pass into engagement with said patella.

15. The patellar cutting guide in accordance with claim 13 wherein said clamp and cutting guide are defined by a body.

16. The patellar cutting guide in accordance with claim 15 wherein said body defines a lever arm and said lever arm and said distal portion of said stop are movable connected to one another, permitting the relative position of said stop to be changed relative to said body.

* * * * *